(12) United States Patent
Zohmann (10) Patent No.: US 8,333,734 B2
(45) Date of Patent: Dec. 18, 2012

(54) FENESTRATED PERIPHERAL NERVE BLOCK NEEDLE AND METHOD FOR USING THE SAME

(75) Inventor: Walter A. Zohmann, Huntsville, UT (US)

(73) Assignee: Walter A. Zohmann, Huntsville, UT (US)

( * ) Notice: Subject to any disclaimer, the term of this patent is extended or adjusted under 35 U.S.C. 154(b) by 620 days.

(21) Appl. No.: 10/613,335

(22) Filed: Jul. 3, 2003

(65) Prior Publication Data

US 2005/0004521 A1    Jan. 6, 2005

(51) Int. Cl.
*A61M 5/178* (2006.01)

(52) U.S. Cl. ......... 604/164.06; 604/164.01; 604/165.01; 604/167.01; 604/168.01

(58) Field of Classification Search .................. 604/158, 604/170.01, 172.02, 170.03, 264, 272, 168.01, 604/164.01, 164.06, 165.01, 167.01
See application file for complete search history.

(56) References Cited

U.S. PATENT DOCUMENTS

| | | | |
|---|---|---|---|
| 2,922,420 A | 1/1960 | Cheng ......................... 128/221 |
| 3,565,074 A | 2/1971 | Foti ............................ 128/214.4 |
| 3,856,009 A | 12/1974 | Winnie ....................... 128/214.4 |
| 4,230,123 A | 10/1980 | Hawkins, Jr. ............... 128/658 |
| 4,308,875 A | 1/1982 | Young ........................ 128/753 |
| 4,317,445 A | 3/1982 | Robinson ................... 128/214.4 |
| 4,629,450 A | 12/1986 | Suzuki et al. ............... 604/164 |
| 4,973,313 A | 11/1990 | Katsaros et al. ............ 604/165 |
| 4,994,036 A | 2/1991 | Biscoping et al. .......... 604/158 |
| 5,106,376 A | 4/1992 | Mononen et al. ........... 604/164 |
| 5,139,485 A * | 8/1992 | Smith et al. ................. 604/158 |
| 5,205,829 A * | 4/1993 | Lituchy ..................... 604/164.08 |
| 5,242,410 A | 9/1993 | Melker ....................... 604/164 |
| 5,250,035 A | 10/1993 | Smith et al. ................ 604/164 |
| 5,304,141 A | 4/1994 | Johnson et al. ............. 604/158 |
| 5,312,360 A | 5/1994 | Behl ........................... 604/164 |
| 5,336,191 A | 8/1994 | Davis et al. ................. 604/165 |
| 5,466,225 A | 11/1995 | Davis et al. ................. 604/165 |
| 5,480,389 A | 1/1996 | McWha et al. ............. 604/165 |
| 5,571,091 A | 11/1996 | Davis et al. ................. 604/165 |
| 5,628,734 A | 5/1997 | Hatfalvi ...................... 604/272 |
| 5,653,694 A * | 8/1997 | Powles et al. .............. 604/240 |
| 5,669,882 A | 9/1997 | Pyles .......................... 604/164 |
| 5,730,749 A | 3/1998 | Battenfield ................. 606/167 |
| 5,800,445 A | 9/1998 | Ratcliff et al. ............. 606/116 |
| 5,836,914 A | 11/1998 | Houghton ................... 604/117 |

(Continued)

FOREIGN PATENT DOCUMENTS

CN    2201946 Y    6/1995

*Primary Examiner* — Victoria P Shumate
(74) *Attorney, Agent, or Firm* — Michael F. Krieger; Kirton McConkie (57) ABSTRACT

A peripheral nerve block needle for facilitating a peripheral nerve block procedure. A needle has several fenestrations along its length to allow an efflux of local anesthetic into a particular fascial compartment to treat a corresponding peripheral nerve despite only roughly approximating the location of such fascial compartment. A needle hub may be attached to the needle so that a backflow of fluid may be observed. A stylet is slidably disposed within the needle and needle hub such that selectively withdrawing the stylet from the apparatus enables a backflow of fluid into the needle hub, from which proper localization of the apparatus may be verified prior to administering local anesthetic. In this manner, local anesthetic may be effectively and efficiently administered to a peripheral nerve with reduced risk of injury to a patient.

9 Claims, 6 Drawing Sheets

U.S. PATENT DOCUMENTS

| | | | |
|---|---|---|---|
| 5,848,996 A * | 12/1998 | Eldor | 604/272 |
| 5,865,806 A | 2/1999 | Howell | 604/164 |
| 5,871,470 A | 2/1999 | McWha | 604/158 |
| 6,245,044 B1 | 6/2001 | Daw et al. | 604/158 |
| 6,558,353 B2 * | 5/2003 | Zohmann | 604/158 |
| 6,613,026 B1 * | 9/2003 | Palasis et al. | 604/272 |
| 6,656,161 B2 * | 12/2003 | Young et al. | 604/168.01 |
| 7,022,109 B1 * | 4/2006 | Ditto | 604/158 |
| 2002/0055715 A1 * | 5/2002 | Young et al. | 604/164.04 |
| 2002/0123723 A1 * | 9/2002 | Sorenson et al. | 604/164.01 |

* cited by examiner

FENESTRATED PERIPHERAL NERVE BLOCK NEEDLE AND METHOD FOR USING THE SAME

BACKGROUND

1. Field of the Invention

This invention relates to innovative needles for facilitating the performance of peripheral nerve blocks and, more particularly, to a novel, atraumatic needle apparatus and method for reducing risks of injury and time associated with administering local anesthetic to a peripheral nerve.

2. Background

A peripheral nerve block is a well-established medical procedure that involves injecting a dose of local anesthetic near and around the nerve or nerve plexus that serves a surgical area. A peripheral nerve block is often used as part of a multimodal analgesia technique where the block is combined with additional medications and methods of medication delivery to target pain at several levels. Peripheral nerve blocks specifically target nociceptive impulses transmitted along peripheral nerves. Other analgesics, for example, non-steroidal anti-inflammatory drugs ("NSAIDs") and opioids, may be used to control pain at the injury site and/or to modify the perception of pain at the cortical level.

Peripheral nerve blocks are highly advantageous for continuous pain relief for several reasons. First, narcotic related side effects are less frequently reported in patients receiving continuous peripheral nerve blocks than in patients receiving epidural or intravenous analgesia. Second, urinary catheters are less frequently required in patients receiving peripheral nerve blocks compared to patients receiving epidural analgesia. Third, patient satisfaction is higher in patients having peripheral nerve blocks than in patients utilizing other analgesic methods. Fourth, the ability of a peripheral nerve block to provide site-specific relief contributes to the overall mobilization of the patient after surgery. Indeed, there is strong clinical evidence that peripheral nerve blocks, especially those administered to the lower extremity, provide superior analgesia compared to other types of analgesia and often result in earlier discharge from the hospital after major joint surgery.

In light of these and other advantages, it is somewhat surprising that only 20-30% of practicing anesthesiologists utilize peripheral nerve blocks as a standard method of analgesia. The most common reasons for avoiding such techniques are time constraints, fear of inadequately anesthetizing an affected nerve, and fear of injuring the affected nerve. Indeed, prior art techniques require a peripheral nerve block needle to be touching or in very close proximity to the affected nerve, without penetrating the nerve or a proximate artery or vein. Positioning the needle in this exact location can be both technically challenging and time consuming.

The major nerves of the lower extremity, including the sciatic and femoral nerves, are unique in that they are contained within well defined fascial compartments. Such lower extremity nerves may be successfully blocked by simply injecting anesthetic into the fascial compartment containing the nerve. Correctly identifying this fascial compartment, however, can be quite challenging.

Accordingly, what is needed is an improved needle for accurately administering anesthetic within a fascial compartment containing an affected lower extremity nerve. Further what is needed is an improved needle for efficiently administering anesthetic within a fascial compartment containing an affected lower extremity nerve. Finally what is needed is a method for properly locating and anesthetizing a fascial compartment containing an affected lower extremity nerve while avoiding intravascular injection and/or inadvertent penetration of the affected nerve.

SUMMARY AND OBJECTS OF THE INVENTION

This invention is a method and apparatus for facilitating peripheral nerve block procedures. A needle comprises a plurality of fenestrations that enable local anesthetic to be administered simultaneously at several points surrounding an affected nerve. A needle further comprises a needle hub attached to a proximal end of the needle in which a backflow of fluid may be observed. A stylet is slidably disposed within the needle and needle hub apparatus such that selectively withdrawing the stylet from the apparatus enables a backflow of fluid into the needle hub, from which proper localization of the apparatus may be verified prior to administering the local anesthetic. In this manner, local anesthetic may be effectively and efficiently administered to a peripheral nerve with reduced risk of injury to a patient.

It is an object of certain embodiments of the present invention to facilitate proper delivery of local anesthetic with respect to an affected peripheral nerve.

Another object of certain embodiments of the present invention is to provide a method for performing a peripheral nerve block that enables effective delivery of local anesthetic to an affected peripheral nerve within a short period of time.

It is yet another object of certain embodiments of the present invention to reduce the risks related to nerve injury and intravascular injection traditionally associated with administration of a peripheral nerve block.

It is yet another object of certain embodiments of the present invention to provide a peripheral nerve block needle apparatus having a stylet that is easily inserted and manipulated.

These and other objects and features of the present invention will become more readily apparent from the following description in which preferred and other embodiments of the invention have been set forth in conjunction with the accompanying drawings and appended claims.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE PREFERRED EMBODIMENTS

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope. The presently preferred embodiments of the invention will be best understood by reference to the drawings, wherein like parts are designated by like numerals throughout.

As used in this specification, the terms "anesthetic" and "analgesia" are used to indicate a chemical composition to induce a loss of sensation with or without loss of consciousness. The term "fenestration" refers to an opening along the surface of a needle that enables a flow of fluid between the needle and a patient. The term "fascial compartment" refers to a intermuscular compartment defined by the fascial layers of at least one muscle.

Figure 1:
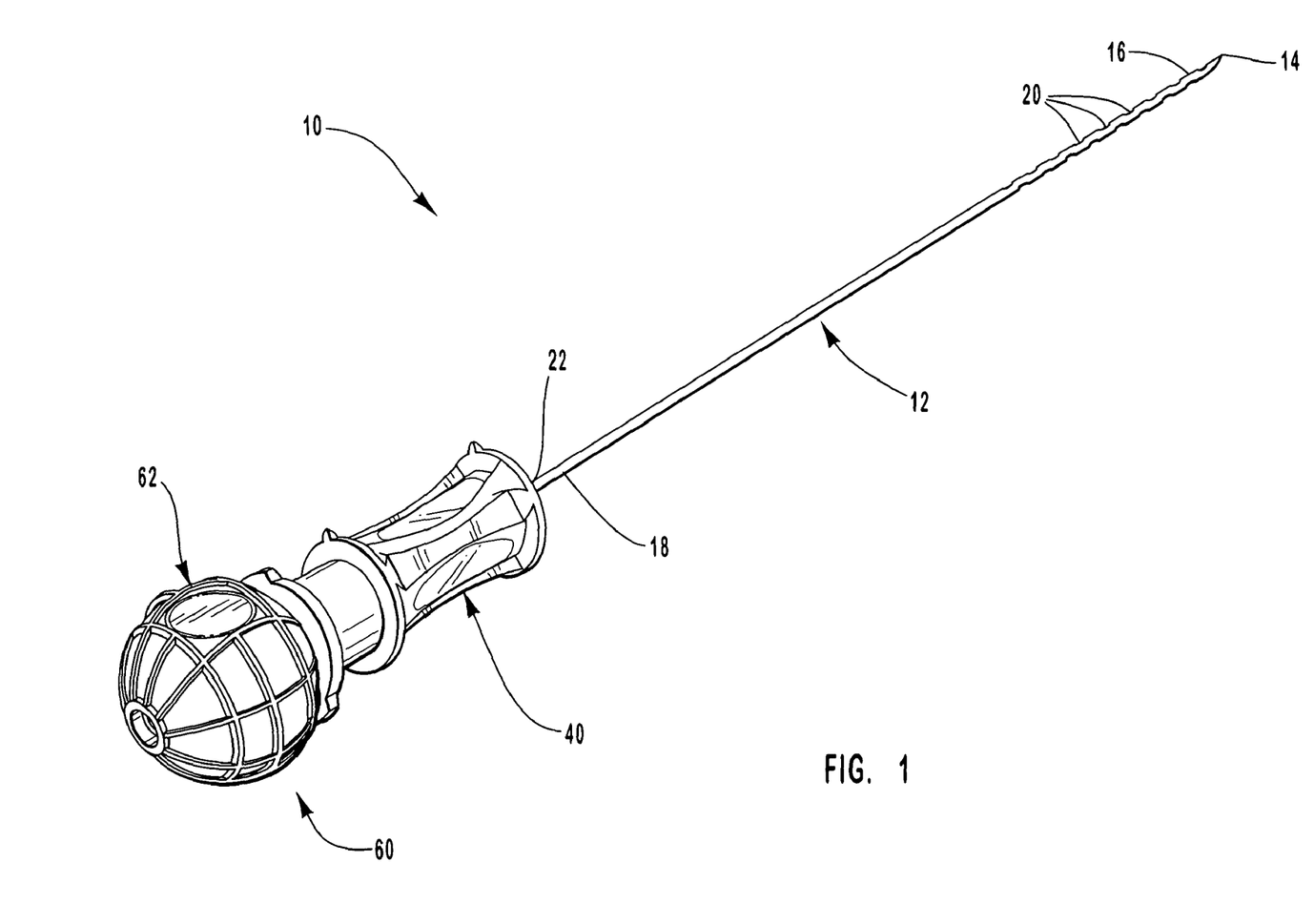
FIG. 1 is a perspective view of a needle apparatus in accordance with the present invention.

Referring to FIG. 1, certain embodiments of the present invention comprise a needle apparatus to facilitate peripheral nerve block procedures. A needle apparatus 10 comprises three main components: a hollow needle component 12, a needle hub component 40, and a stylet component 60. A hollow needle component 12 may comprise a plurality of fenestrations 20 disposed longitudinally thereon to permit a flow of fluid between the needle 12 and a patient. Fenestrations 20 are preferably located proximate a distal end 16 of a needle 12. For example, fenestrations 20 located on a needle 12 5.0 inches in length are preferably contained along a distance measured from the tip 14 to about 1.785 inches along the length of the needle 12.

A hollow needle hub component 40 may be coupled to a needle 12 mechanically by heat, an adhesive, a retaining mechanism, a secure pressure fit, or by any other means known to those in the art. A stylet component 60, comprising a stylet 70 and a stylet cap 62, may be freely inserted, removed and rotated within the combined needle 12 and needle hub 14 structure, and may be selectively retained therein by a pressure fit, a selective release mechanism, or by any other means known to those in the art.

Figure 2:
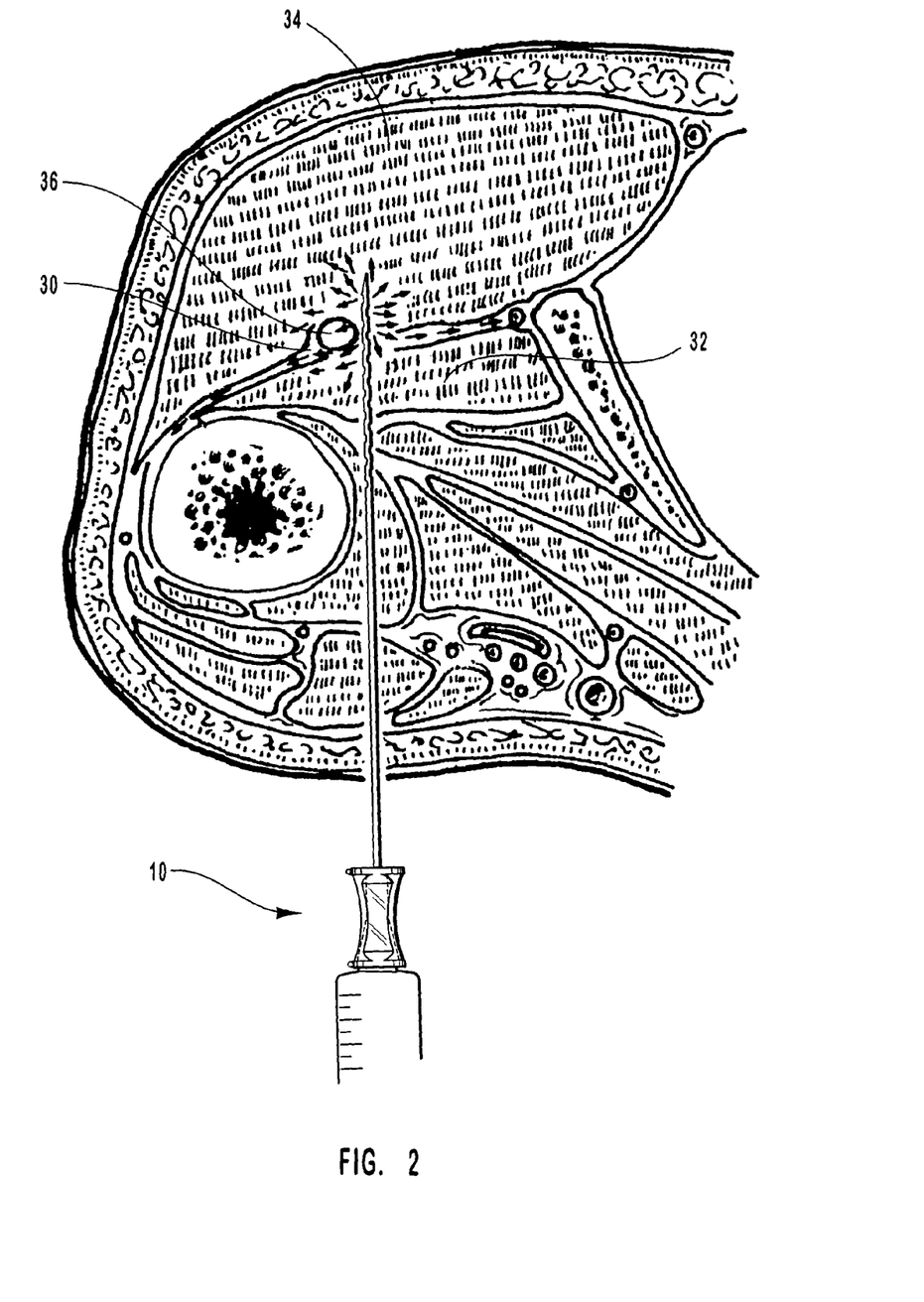
FIG. 2 is a cross-sectional view of a human thigh depicting the location of the sciatic nerve within a fascial compartment.

Referring now to FIG. 2, a fascial compartment 30 containing lower extremity nerves may comprise only a few millimeters in width. For example, a discrete fascial compartment 30 of only a few millimeters is located between the semitendinosis muscle 32 and the biceps femoris muscle 34. This fascial compartment 30 houses the sciatic nerve 36, one of two major lower extremity nerves. Fenestrations 20 are spaced at relatively small intervals along the needle 12 in order to maximize an even distribution of local anesthetic to any particular fascial compartment 30, including particularly narrow compartments such as that housing the sciatic nerve 36. Fenestrations 20 are preferably located within 0.17 inches, and most preferably within within one to two millimeters, of each other for this purpose. Additionally, fenestrations 20 may occupy alternating sides of a needle 12 to facilitate even distribution of local anesthetic to an affected peripheral nerve.

As fascial compartments 30 are less resistant to the flow of local anesthetic than surrounding muscle, a greater efflux of local anesthetic is observed through fenestrations 20 corresponding to fascial compartments than through fenestrations 20 located intramuscularly. Once introduced into a fascial compartment 30, local anesthetic passively flows to a peripheral nerve contained therein. In this manner, the needle apparatus 10 of the present invention may be introduced into a dermal area roughly corresponding to a desired fascial compartment, while ensuring effective and safe administration of local anesthetic to an appropriate peripheral nerve. Indeed, since a precise location of a peripheral nerve need not be pinpointed in order to effectively anesthetize the nerve so long as a portion of the fascial compartment 30 containing the nerve is penetrated, and since local anesthetic introduced into an appropriate fascial compartment 30 passively flows to the nerve contained therein even absent locating the needle 12 immediately adjacent the nerve, it is possible to administer a peripheral nerve block without incurring substantial risk of injury to the nerve. A peripheral nerve block may also be accomplished in less time since only a rough determination of the location of the fascial compartment 30 containing the appropriate peripheral nerve is required. These features of the present invention are highly beneficial to practitioners performing lower extremity peripheral nerve block procedures and to their patients, as the time and risks associated with such procedures are greatly reduced.

Figure 3:
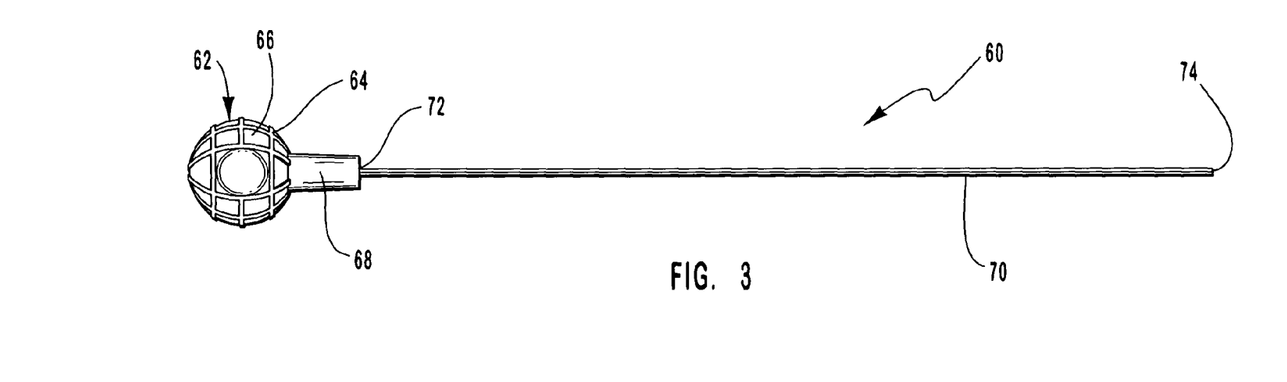
FIG. 3 is a side view of the stylet associated with the needle apparatus of the present invention.

Referring now to FIG. 3, a stylet component 60 comprises a stylet 70 having a proximal end 72 and a distal end 74. The term proximal as used herein connotes proximate to the "main body" of needle apparatus 10, or in other words, nearer the portion of needle apparatus 10 that connects to a syringe. The term "distal" connotes a position removed from the main body of needle apparatus 10 or in other words, nearer the tip 14 of the needle apparatus 10. A stylet 70 has a diameter and a length. The length and diameter of the stylet 70 are sufficient to occlude a hollow needle 12 and its associated fenestrations 20 when the stylet 70 is inserted into the needle 12.

Figure 6:
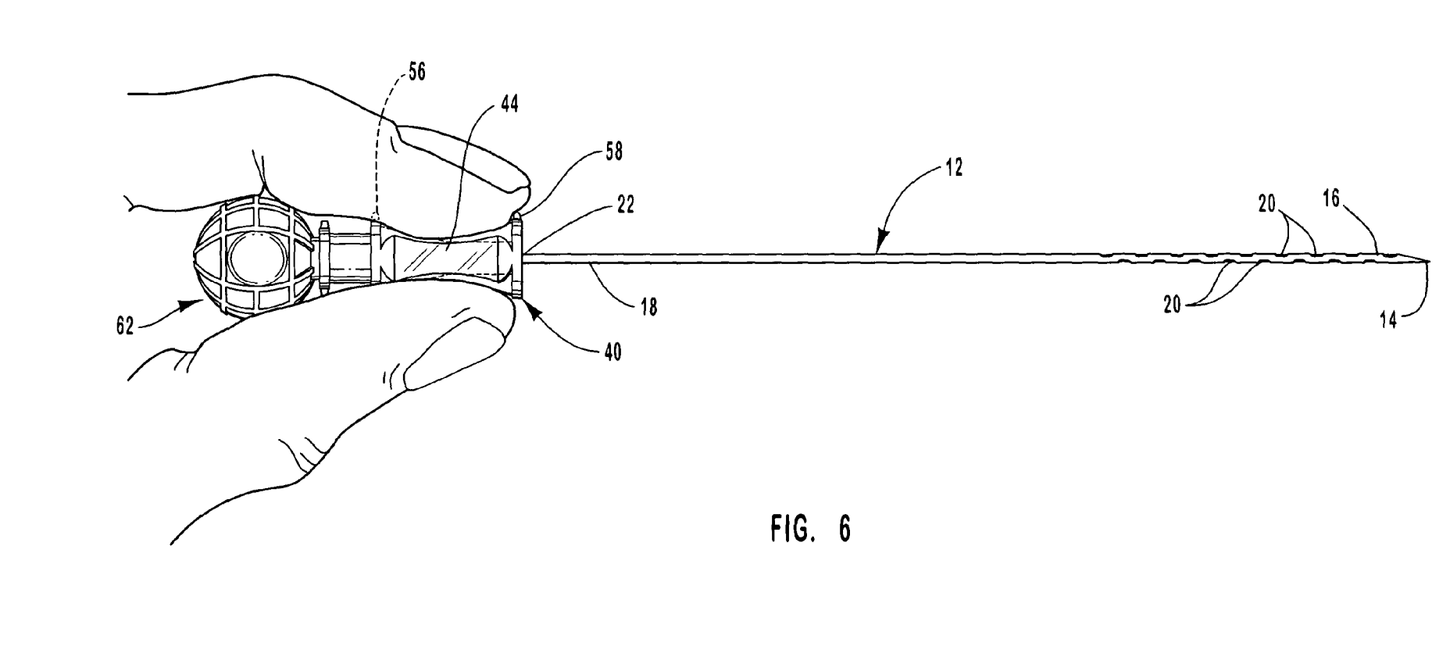
FIG. 6 is a perspective view of the needle hub with the user's finger in contact with the raised portions for verifying the orientation of fenestrations present on a needle.
Figure 7:
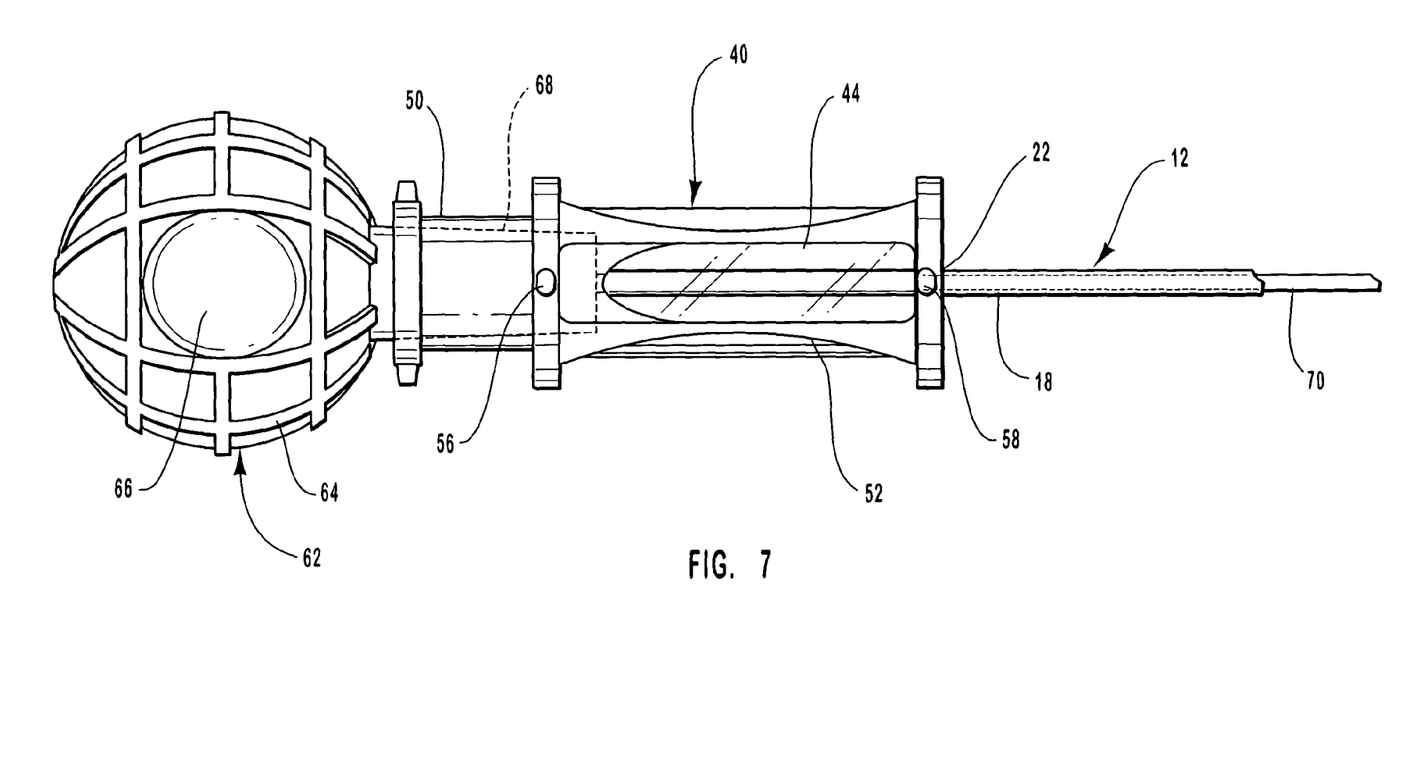
FIG. 7 is an enlarged perspective view of the needle hub with a magnifying window and inserted stylet.

A stylet cap 62 has a generally spherical shape with raised portions 64 and flat areas 66 distributed throughout its surface. The generally uniform shape of the stylet cap 62 allows the stylet cap 62 to be gripped with a conventional or uniform grip from almost any angle. Raised portions 64 and flat areas 66 of a stylet cap 62 allow the stylet cap 62 to be manipulated more easily, even when the user is wearing surgical gloves. A stylet cap 62 has a cap nose component 68 disposed around the stylet 70 where the stylet 70 communicates with the stylet cap 62. A cap nose component 68 is frusco-conical in shape with the broader base of the cone being adjacent to the stylet cap 62. The diameter of a cap nose 68 allows it to slide into and fit securely with hollow needle hub 40, as shown in FIGS. 6 and 7. A stylet cap 62 and needle hub 40 create a pressure fit that allows a stylet 70 to be rotated about its axis and still be secured by a pressure fit with the needle hub 40. A stylet cap 62 does not need to be rotated to a particular orientation to create the pressure fit.

The stylet component 60 of the present invention offers several advantages. First, the stylet 70 reinforces a hollow needle 12 as the needle 12 is being inserted, positioned or retracted. Second, as mentioned above, a stylet 70 occludes fenestrations 20 on the needle 12. Occlusion of fenestrations 20 is particularly necessary in cases where the needle 12 must be repositioned during a procedure. Additionally, the stylet 70, when withdrawn, indicates whether the needle 12 was bent during entry.

In addition to the advantages above, the stylet 70 of the present invention provides a stylet cap 62 that makes it easier to see and manipulate the stylet 70 than prior art stylet caps. The stylet cap 62 of the present invention reduces the likelihood that an anesthesiologist or other practitioner will mishandle or fumble with the stylet 70, thereby reducing both the incidence of unnecessary trauma to tissue and the time required to complete a procedure. For example, during a peripheral nerve block procedure, an anesthesiologist or other practitioner may need to withdraw and reinsert the needle 12 until he or she can verify that the needle 12 is not located intravascularly. Once verified, the anesthesiologist or other practitioner may need to promptly reinsert the stylet 70 to occlude fenestrations 20. The stylet cap 62 of the present invention facilitates the anesthesiologist's efforts to respond promptly, once the anesthesiologist has verified proper needle placement. The stylet cap 62 provides improved handling of the stylet 70 and allows the stylet 70 to be more quickly positioned. The stylet 70 does not have to be aligned in a particular position relative to needle hub 40, as do prior art devices.

The stylet 70 slides inside a hollow needle 12 through a needle hub 40 until the stylet cap 62 contacts the needle hub 40. The cap nose component 68 slides into and contacts interior walls of the needle hub 40, thereby creating a pressure fit between the cap nose 68 and the broad opening 46 of the needle hub 40. The spherical shape of the stylet cap 62 obstructs the broad opening 46 of the needle hub 40.

Figure 4:
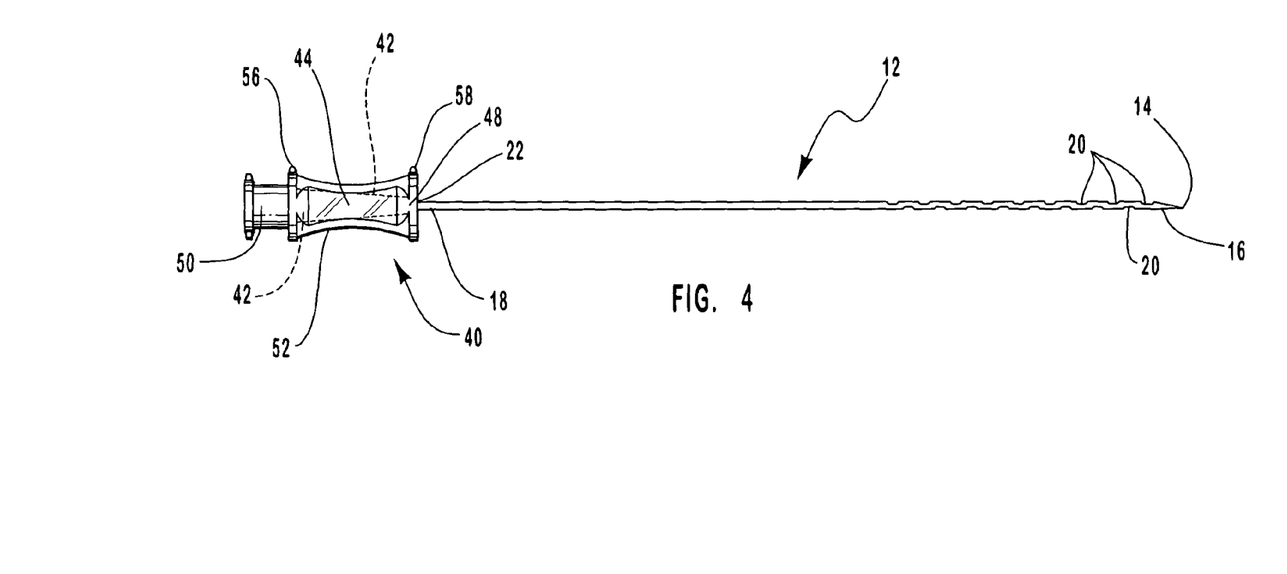
FIG. 4 is a side view of the needle and needle hub of the present invention.

Referring now to FIG. 4, the needle apparatus 10 of the present invention further comprises a hollow needle 12 having a length and diameter suitable for injection of anesthetic into a fascial compartment surrounding a peripheral nerve. The length of a needle is bounded by an occluded tip 14 at a distal end 16, and an intake opening 22 at a proximal end 18. Fenestrations 20 are longitudinally disposed along the length of the needle 12, and are preferably isolated on a distal end 16 of the needle 12 to facilitate an effective amount of efflux into a desired fascial compartment or other area proximate an affected peripheral nerve. Fenestrations 20 may be isolated along one side of a needle 12, may alternate between sides of a needle 12, or may occupy more than one side of a needle 12. A needle hub 40 is disposed around the proximal end 18 of the needle 12, and is configured to receive a syringe.

A needle hub 40 is hollow, defined by a funnel 42 having two openings, a first narrow opening 48 communicating with the needle intake opening 22, and a broad opening 46 at the hub's proximate end. A cap nose component 68 of a stylet cap 62 may be inserted into the broad opening 46 of the funnel 42 by a pressure fit. The broad opening 46 comprises a shape corresponding to the stylet cap nose 68 to allow such a pressure fit. In one embodiment, the broad opening 46 is substantially cylindrical and tubular, thereby allowing a frusco-conical shaped stylet cap nose 68 to form a pressure fit therein. A needle hub 40 may also provide an extended opening 50.

A needle hub 40 further comprises a finger grip 52 disposed about the funnel 42. A finger grip 52 may comprise a plurality of sides and a length and diameter which allows the finger grip 52 to be easily manipulated between the thumb and forefinger. The sides of the finger grip 52 can be slightly concave to facilitate handling. Additionally, a needle hub 40 may incorporate a magnifying window 44. Such magnifying window 44 reveals the content of the needle hub 40 in magnified view. In one embodiment, the funnel 42 is magnified so that any fluid passing into or out of the funnel 42 is more easily viewed by the user.

Figure 5:
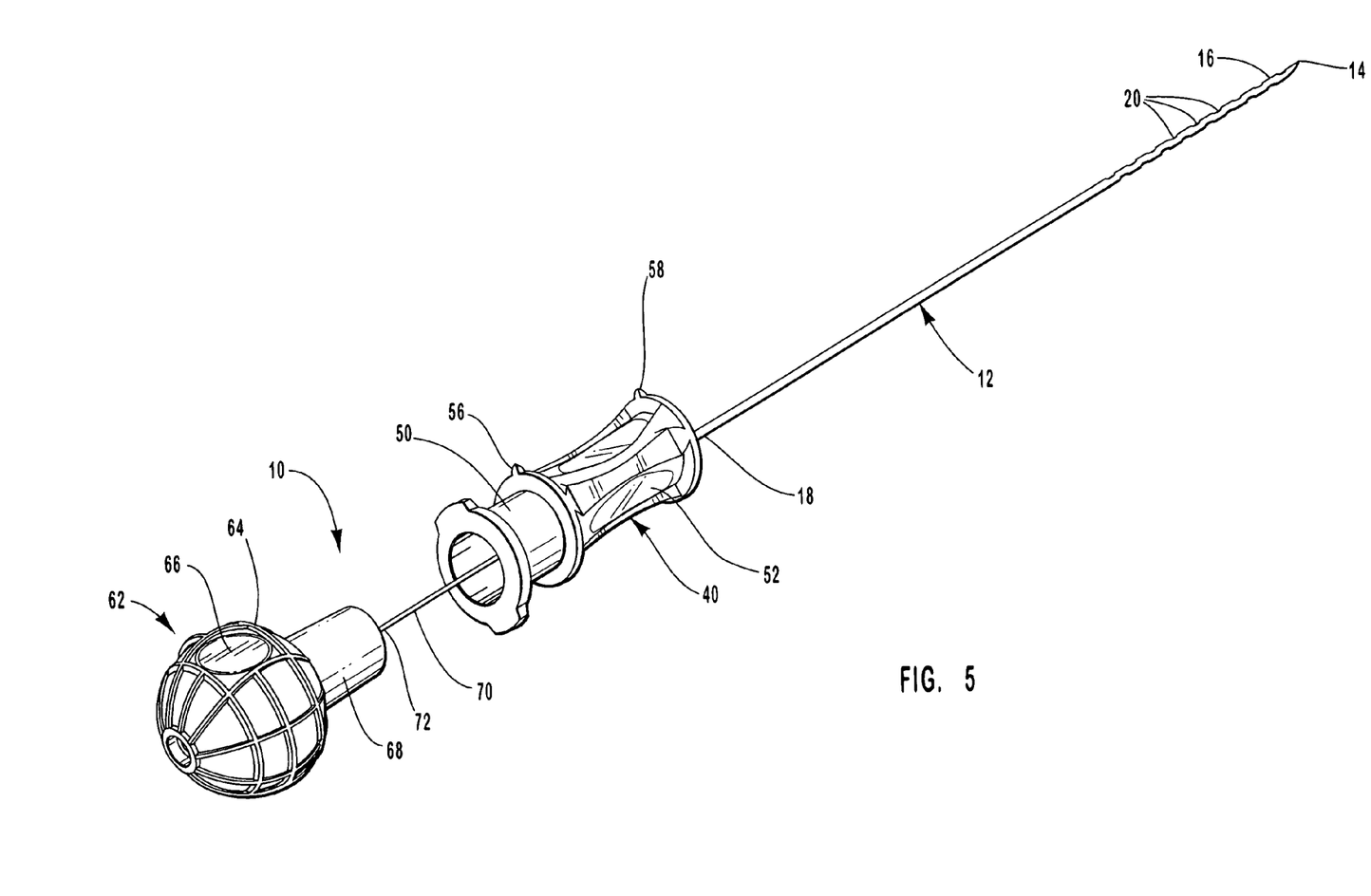
FIG. 5 is a perspective view of the stylet cap and stylet partially inserted and in alignment with the needle hub and needle of the present invention.

In one embodiment of the present invention, a needle hub 40 also provides fenestration indicators 56 and 58. Fenestration indicators 56 and 58 comprise raised portions of the needle hub 40 that correspond to the relative position of fenestrations 20 located along a particular side of a needle 12. In this manner, orientation of fenestrations 20 can be observed even when fenestrations 20 are not in view. This allows a user to remain aware of the direction of the release or uptake of fluid through fenestrations 20. In a preferred embodiment, fenestration indicators 56 and 58 are raised from the surface of the needle hub 40 to provide visual and/or tactile verification of fenestration 20 orientation, as shown in FIG. 5.

What is claimed is:

1. A needle apparatus for administering a peripheral nerve block, said needle apparatus comprising:
   a hollow needle having a plurality of fenestrations proximate a distal end of said hollow needle, structured to allow location of multiple fenestrations within a fascial compartment during injection to achieve an even distribution of local anesthetic within a fascial compartment, wherein the fenestrations are arranged in two columns on opposing sides of the hollow needle, wherein the fenestrations in each column are spaced at intervals within one to two millimeters within the column, and wherein the fenestrations of one column are offset in an alternating pattern with respect to the fenestrations of the other column so as to increase the likelihood that at least one fenestration is positioned within a fascial compartment when the hollow needle is injected to administer a greater efflux of local anesthetic inside the fascial compartment through the at least one fenestration positioned within the fascial compartment than through fenestrations located intramuscularly outside the boundaries of the fascial compartment;
   a needle hub having a hollow interior disposed about a proximate end of said hollow needle; and
   a stylet cap coupled to a proximate end of a stylet, wherein said stylet is freely slidable inside said hollow needle and needle hub, such that selectively withdrawing the stylet from the needle hub enables a back flow of fluid into the needle hub from which proper localization of the apparatus may be verified prior to administering the local anesthetic and wherein said stylet cap creates a releasably secure pressure fit with said needle hub upon full insertion of said stylet into said hollow needle.

2. The needle apparatus of claim 1, wherein said fenestrations are longitudinally disposed along the opposing sides of said hollow needle.

3. The needle apparatus of claim 2, wherein said needle hub further comprises at least one fenestration indicator disposed about said needle hub, said fenestration indicator capable of providing visual and tactual verification by a user of an orientation of said fenestrations.

4. The needle apparatus of claim 1, wherein said needle hub further comprises a magnifying window disposed within said needle hub, wherein said magnifying window provides a magnified view of said hollow interior of said needle hub.

5. A needle apparatus for administering a peripheral nerve block, said needle apparatus comprising:
   a hollow needle having a plurality of fenestrations proximate a distal end of said hollow needle, structured to allow location of multiple fenestrations within a fascial compartment during injection to achieve an even distribution of local anesthetic within a fascial compartment, wherein the fenestrations are arranged in two columns on opposing sides of the hollow needle, wherein the fenestrations in each column are spaced at intervals within one to two millimeters within the column, and wherein the fenestrations of one column are offset in an alternating pattern with respect to the fenestrations of the other column so as to increase the likelihood that at least one fenestration is positioned within a fascial compartment when the hollow needle is injected to administer a greater efflux of local anesthetic inside the fascial compartment through the at least one fenestration positioned within the fascial compartment than through fenestrations located intramuscularly outside the boundaries of the fascial compartment;

a needle hub disposed about a proximate end of said hollow needle, said needle hub having at least one fenestration indicator disposed about said needle hub, wherein said fenestration indicator is capable of providing visual and tactual verification by a user of an orientation of said fenestrations; and a stylet cap disposed about a proximate end of a stylet, said stylet cap capable of forming a releasably secure, axially rotatable pressure fit with said needle hub, wherein said stylet is capable of freely sliding inside said hollow needle and needle hub, and wherein said stylet occludes said fenestrations when fully inserted into said hollow needle.

6. The needle apparatus of claim 5, wherein said needle hub further comprises a magnifying window disposed within said needle hub, wherein said magnifying window provides a magnified view of an interior of said needle hub.

7. A method for anesthetizing an affected peripheral nerve, said affected peripheral nerve being contained within a corresponding fascial compartment, wherein said fascial compartment comprises a fascial membrane, said method comprising:

identifying a dermal area of a patient substantially corresponding to said affected peripheral nerve;

inserting a fenestrated needle into said dermal area, said fenestrated needle comprising a plurality of fenestrations proximate a distal end of said hollow needle, structured to allow location of multiple fenestrations within the fascial compartment during injection to achieve an even distribution of local anesthetic within a fascial compartment, wherein said plurality of fenestrations are arranged in two columns on opposing sides of the hollow needle, wherein the fenestrations in each column are spaced at intervals within one to two millimeters within the column, and wherein the fenestrations of one column are offset in an alternating pattern with respect to the fenestrations of the other column so as to increase the likelihood that at least one fenestration is positioned within a fascial compartment when the hollow needle is injected to administer a greater efflux of local anesthetic inside the fascial compartment through the at least one fenestration positioned within the fascial compartment than through fenestrations located intramuscularly outside the boundaries of the fascial compartment;

advancing said fenestrated needle slowly through said dermal area and said fascial membrane, whereby at least one of said fenestrations is located within said fascial compartment;

withdrawing a stylet disposed within said fenestrated needle to verify proper placement of said fenestrated needle; and injecting local anesthetic through said fenestrated needle to induce an efflux of local anesthetic into said fascial compartment while minimizing flow of anesthetic outside the boundaries of the fascial compartment and a corresponding anesthetic block at said affected peripheral nerve.

8. The method of claim 7, wherein said fenestrated needle further comprises a needle hub disposed about a proximate end of said fenestrated needle.

9. The method of claim 8, wherein said withdrawing a stylet further comprises observing a backflow of fluid within said needle hub to verify that said fenestrated needle is not located intravascularly.

* * * * *